United States Patent [19]

Inaba et al.

[11] Patent Number: 5,097,080
[45] Date of Patent: Mar. 17, 1992

[54] PROCESS FOR PREPARING 4,4'-DIHYDROXYBIPHENYL

[75] Inventors: Masashi Inaba; Norioki Mine; Mamoru Mizutani, all of Mie, Japan

[73] Assignee: Mitsubishi Petrochemical Co., Ltd., Tokyo, Japan

[21] Appl. No.: 625,068

[22] Filed: Dec. 10, 1990

[30] Foreign Application Priority Data

Dec. 15, 1989 [JP] Japan .................................. 1-324037

[51] Int. Cl.$^5$ ........................ C07C 37/50; C07C 39/15
[52] U.S. Cl. ................................................... 568/805
[58] Field of Search ............................. 568/805, 730

[56] References Cited

U.S. PATENT DOCUMENTS 4,891,453  1/1990  Tanaka et al. .................. 568/730
4,950,808  8/1990  Kowalczik et al. ............. 568/730

*Primary Examiner*—Werren B. Lone
*Attorney, Agent, or Firm*—Oblon, Spivak, McClelland, Maier & Neustadt

[57] ABSTRACT

A process for preparing 4,4'-dihydroxybiphenyl is disclosed, which comprises debutylation of 3,3', 5,5'-tetra-t-butyl-4,4'-dihydroxybiphenyl in an organic solvent in the presence of an acid catalyst, wherein said debutylation is carried out in the presence of water and/or a lower alcohol. The desired product can be obtained at a high purity in a high yield.

20 Claims, No Drawings

PROCESS FOR PREPARING 4,4'-DIHYDROXYBIPHENYL

FIELD OF THE INVENTION

This invention relates to process for preparing 4,4'-dihydroxybiphenyl (hereinafter abbreviated as BPL) and, more particularly to a process for economically preparing BPL having high purity.

BACKGROUND OF THE INVENTION

BPL has lately attracted considerable attention as a starting material of heat resistant engineering plastics. Known processes for preparing BPL include (1) alkali fusion of diphenyl disulfonic acid, (2) hydrolysis of dibromodiphenyl, and (3) oxidative dimerization of 2,6-di-t-butylphenol followed by debutylation. The former two processes not only need severe reaction conditions but have difficulty in separating the product from a large quantity of inorganic salts used in the reaction. Accordingly, the process comprising oxidative dimerization of 2,6-di-t-butylphenol is the most preferred for industrial production of BPL.

This process, however, involves problems discussed below which are accompanied by debutylation subsequent to the oxidative dimerization. It is known that 3,3',5,5'-tetra-t-butyl-4,4'-dihydroxybiphenyl (hereinafter abbreviated as TBBPL) which is obtained by oxidative dimerization of 2,6-di-t-butylphenol can be debutylated by using an acid catalyst, e.g., sulfuric acid and p-toluenesulfonic acid, in an organic solvent. Consecutively proceeding, the debutylation reaction does not complete when conducted at a low temperature, and intermediate products, such as mono-, di-, tri-, or tetra-t-butyldihydroxybiphenyl remain in the reaction mixture, resulting in a reduction of BPL yield. Therefore, the debutylation reaction is usually carried out in a high-boiling solvent at a temperature elevated up to 200° C. or more in order to complete the reaction. According to the process disclosed in JP-A-61-200935 or JP-B-62-135 (the terms "JP-A" and JP-B" as used herein mean an "unexamined published Japanese patent application" and an "examined Japanese patent publication", respectively), for example, debutylation is carried out in diphenyl ether as a high-boiling solvent in the presence of p-toluenesulfonic acid at a temperature elevated to 250° C.

Where a high-boiling solvent is used as described above, such a process is uneconomical and inefficient for industrial production to remove the solvent attached to the resulting crude BPL crystals. Moreover, the high-temperature reaction causes thermal deterioration of BPL, making the hue of the final product poor.

On the other hand, where a large quantity of a catalyst is used to attempt to complete debutylation under a mild temperature condition without using a high-boiling solvent, the quality of BPL, particularly the hue is deteriorated with an increase of the catalyst amount.

SUMMARY OF THE INVENTION

An object of the present invention is to provide a process for economically and efficiently preparing BPL of high purity in high yield.

As a result of extensive investigations, it has now been found that the above object of this invention is accomplished by carrying out debutylation of TBBPL in the presence of water and/or a lower alcohol.

The present invention relates to a process for preparing BPL which comprises debutylation of TBBPL in an organic solvent in the presence of an acid catalyst, wherein said debutylation is carried out in the presence of water and/or a lower alcohol.

DETAILED DESCRIPTION OF THE INVENTION

TBBPL which can be used as a starting material of debutylation in the present invention is obtained by oxidative dimerization of 2,6-di-t-butylphenol. The manner of oxidative dimerization of 2,6-di-t-butylphenol is not particularly restricted. The resulting TBBPL is preferably once isolated and purified for improving yield and quality of BPL, but the oxidative dimerization may be directly followed by debutylation.

The organic solvent which can be used for debutylation is not strictly limited in kind. However, since debutylation must be conducted at a temperature of 100° C. at the lowest, solvents having a boiling point of 100° C. or higher are preferred. Further, solvents capable of dissolving the starting TBBPL to a relatively good extent are preferred.

Examples of suitable solvents include aromatic compounds, e.g., chlorobenzene, toluene, xylene, ethylbenzene, isopropylbenzene, t-butylbenzene, diethylbenzene, diisopropylbenzene, naphthalene, and methylnaphthalene; paraffins, e.g., decane, undecane, and tridecane; and paraffin mixtures, e.g., light oil. These solvents may be used either individually or in combination of two or more thereof.

The solvent is used in an amount of from 0.5 to 10 parts by weight, and preferably from 1 to 5 parts by weight, per part by weight of TBBPL.

Acid catalysts which can be used for debutylation include sulfonic acids, e.g., p-toluenesulfonic acid and sulfuric acid, and Lewis acids, e.g., aluminum trichloride, aluminum phenoxide compounds, and aluminum alcoholates. The acid catalyst is used in an amount of from 0.1 to 20% by weight, and preferably from 1 to 10% by weight, based on the starting TBBPL.

In the present invention, water, a lower alcohol, or a mixture thereof is added to the reaction system. The lower alcohol to be added includes methanol, ethanol, and propanol. The amount of water and/or a lower alcohol to be added is in the range of at least 0.1 times, generally from 0.5 to 10 times, and preferably from 1 to 5 times, the weight of the acid catalyst.

Water and/or alcohols may be added separately but are desirably added together with the acid catalyst because isobutene gas by-produced would be effectively driven out of the reaction system, which leads to an increased reaction rate and an increased yield. Water and/or alcohols added to the reaction system vaporize almost in an instant and are recovered outside the system.

Use of an acid catalyst which is a highly hygroscopic solid and has poor fluidity, such as p-toluenesulfonic acid and benzenesulfonic acid, has been accompanied by difficulties such that addition of such a solid catalyst to a reaction vessel had to be done very quickly. Such difficulties can be eliminated by adding these acid catalysts as dissolved in water or an alcohol.

According to the process of the present invention, the reaction can be effected at a temperature ranging from 100° to 200° C., and preferably from 130° to 180° C. A reaction at a temperature lower than 100° C. only requires a longer reaction time. Reaction temperatures higher than 200° C. cause deterioration or coloring of the product, making it difficult to obtain white and high purity BPL.

The reaction time, though varying depending on the temperature and other conditions, usually ranges from about 1 to 10 hours, and preferably from about 3 to 7 hours. Too a long reaction time results in a reduction in quality, such as a hue.

The reaction is usually carried out under normal pressure or, if desired, under pressure or under reduced pressure. A preferred reaction pressure ranges from 100 Torr to 2 atm.

The reaction is usually carried out by supplying the starting material and the solvent to the reaction system, heating the resulting mixture to the predetermined temperature and then adding the acid catalyst and water or alcohols thereto. The reaction starts almost in an instant to generate isobutene gas and simultaneously form a low polymer of isobutene. In order to increase a reaction yield, it is necessary to efficiently drive them out of the reaction system.

It is preferable to conduct the debutylation reaction while distilling the solvent. Where the solvent to be used has a boiling point of not higher than 200° C., the reaction solution may be kept boiling while recovering solvent vapors by means of a condenser, etc. When the reaction is effected while bubbling an inert gas, such as nitrogen, in the reaction solution, the solvent can be distilled without boiling the solution.

A distillation rate is in the range of from 0.05 to 20 times, and preferably from 1 to 10 times, the weight of the solvent initially supplied, per hour. The distillation rate less than 0.05 times does not effectively increase the reaction yield. The distillation rate higher than 20 times makes it difficult to supply the heat to the reaction system because of a huge amount of latent heat of vaporization of the solvent. However, when the distillation amount of solvent is too large and the reaction mixture is too concentrated, because there are some problems such as the deterioration of product and the difficulty of stirring, it is necessary to retain the solvent in the reaction system in an amount at least equal to the weight of BPL.

Isobutene by-produced during the reaction, which is gaseous at room temperature, is discharged together with the solvent vapors and separated from the solvent on condensation of the solvent. Although the solvent distilled off the reaction system contains the low polymer of isobutene, the solvent and the low polymer separate from each other to form two layers on the condensation of the solvent.

In the case where the reaction is carried out while distilling the solvent, it is desirable to supply the solvent to the reaction system during reaction in order to make up the loss of the solvent with the progress of distillation. The solvent to be supplied may be either the one which has been distilled off the reaction system and recovered or a fresh one. In the former case, the solvent to be recycled is used by removing a separated layer of a low polymer of isobutene which is present in the recovered solvent in a small amount.

Since the debutylation reaction is an endothermic reaction, the solvent to be supplied is preferably preheated so as not to decrease the reaction temperature. It is particularly preferred that the solvent to be supplied be heated above the reaction temperature so as to serve as a heat source for the reaction, whereby the reaction can be accelerated and the yield can be increased. In this case, the solvent to be supplied is heated to a temperature of from 100° to 250° C., and preferably from the reaction temperature up to a temperature higher than the reaction temperature by 50° C., with the pressure being above the reaction pressure, selected from the range of from 1 to 10 kg/cm$^2$.

The solvent to be supplied may be either liquid or gaseous, but is preferably heated to a gaseous phase from the standpoint of heat supply. The solvent having the gaseous phase can be supplied by blowing into the reaction mixture.

The present invention is now illustrated in greater detail by way of Examples, but it should be understood that the present invention is not construed as being limited thereto. In Examples, all the percents are by weight unless otherwise indicated.

EXAMPLE 1

In a 300 ml four-necked round flask was charged a solution of 50 g (0.121 mol) of TBBPL obtained by oxidative dimerization of 2,6-di-t-butylphenol in 50 g of ethylbenzene. The flask was equipped with a thermometer, a tube for introducing nitrogen gas, a stirring blade, a distilling trap with stop cock, and a condenser. After displacing the atmosphere in the flask with nitrogen, the flask was soaked in an oil bath heated to 170° C., and the temperature was raised in a nitrogen atmosphere with stirring. When the inner temperature reached 80° C., a solution of 3.75 g (0.02 mol) of p-toluenesulfonic acid in 7.5 g (0.42 mol) of water was added thereto dropwise. Distillation of water took place simultaneously with the dropwise addition, and water was pooled in the reservoir. The heating was continued, and the temperature was maintained at 140° C., at which the mixture was allowed to react for 5 hours.

After completion of the reaction, the reaction mixture was cooled to 70° C. The precipitated crystals of BPL were collected by filtration, washed with 50 g of ethylbenzene, and dried to obtain 21.2 g (yield: 93.5%) of 4,4'-dihydroxybiphenyl as white crystals.

Gas chromatography of the resulting product revealed a purity of 99.7%. To evaluate a hue of the product, an absorbance of a 5% methanolic solution of the crude BPL at 400 nm was measured with a spectrophotometer "UV-2100" manufactured by Shimazu Seisakusho Ltd. (hereinafter the same). The absorbance in a 10 mm thick quartz cell was 1.519.

EXAMPLE 2

The same procedures as in Example 1 were repeated, except for replacing water with methanol. As a result, 21.3 g (yield: 94.0%) of BPL was obtained. The resulting product was found by gas chromatography to have a purity of 99.7%. A methanolic solution of the crude BPL had an absorbance of 0.310.

COMPARATIVE EXAMPLE 1

The same procedures as in Example 1 were repeated, except for replacing p-toluenesulfonic acid as dissolved in water with powderous p-toluenesulfonic acid. As a result, 19.7 g of BPL was obtained in a yield of 86.9%. Purity of the product was found by gas chromatography to be 99.6%. The absorbance of a methanolic solution of the crude BPL was 1.729.

COMPARATIVE EXAMPLE 2

The same procedures as in Example 1 were repeated, except for replacing water with ethylene glycol. As a result, 1.4 g of BPL was obtained in a yield of 6.2%. Purity of the product as measured by gas chromatography was 97.6%, and the absorbance of a methanolic solution of the crude BPL was 0.119.

EXAMPLE 3

The same procedures as in Example 1 were repeated, except for replacing water with methanol and changing the temperature of the oil bath to 175° C. During the reaction, the solvent was recovered in the distilling trap. After removing the methanol at the initial boiling point, the recovered ethylbenzene from which a separate layer of a low polymer of isobutene was removed was recycled to the reaction vessel so as to maintain the liquid level of the reaction vessel almost constant. The distillation rate of ethylbenzene was 350 g/hr.

After completion of the reaction, the reaction mixture was cooled to room temperature, and the precipitated BPL crystals were collected by filtration, washed with ethylbenzene and water, and dried to obtain 21.1 g (yield: 93%) of BPL crystals. The purity of the product as measured by gas chromatography was 99.7%, and the absorbance of a 5% methanol solution of the product was 0.105.

EXAMPLE 4

In the same reaction apparatus as used in Example 3 were charged 50 g (0.12 mol) of TBBPL and 50 g (0.37 mol) of diethylbenzene (boiling point: 180° C.), and the mixture was externally heated in an oil bath at 210° C. At the point where the solution began to boil, a solution of 3.75 g (0.02 mol) of p-toluenesulfonic acid in 7.5 g of methanol was added thereto to commence a reaction. The reaction temperature at this point was 184° C., at which the reaction was continued for 3 hours. The solvent recovered in the reservoir was recycled in the same manner as in Example 3 to maintain the liquid level substantially constant. The distillation rate of diethylbenzene was 290 g/hr.

After completion of the reaction, the reaction mixture was worked-up in the same manner as in Example 1 to obtain 21.3 g (yield: 94%) of BPL having a purity of 99.8%. The absorbance of a 5% methanol solution of the product was 0.180.

EXAMPLE 5

In the same reaction apparatus as used in Example 3, except that the volume of the flask was 1 l, were charged 200 g (0.49 mol) of TBBPL and 200 g (1.89 mol) of ethylbenzene, and the mixture was externally heated in an oil bath at 175° C. At the point when the solution began to boil, a solution of 15 g (0.078 mol) of p-toluenesulfonic acid in 30 g of methanol was added thereto to commence a reaction. After the commencement, ethylbenzene was recovered at a distillation rate of 1400 g/hr.

Separately, a helical tube made of a copper tube having an inner diameter of 8 mm was put in an oil bath at 175° C. to prepare a vapor heating apparatus. Fresh ethylbenzene was fed into the tube at the same rate as the distillation rate by means of a constant delivery pump to prepare vapor of ethylbenzene, which was blown into the reaction system to conduct the reaction at a reaction temperature of 140° C. for 3 hours.

There was obtained 81.6 g (yield: 90%) of BPL having a purity of 99.7% as measured by gas chromatography. The absorbance of a 5% methanol solution of the product was 0.167.

While the invention has been described in detail and with reference to specific examples thereof, it will be apparent to one skilled in the art that various changes and modifications can be made therein without departing from the spirit and scope thereof.

What is claimed is:

1. A process for preparing 4,4'-dihydroxybiphenyl which comprises debutylation of 3,3',5,5'-tetra-t-butyl-4,4'dihydroxybiphenyl in an organic solvent in the presence of an acid catalyst selected from the group consisting of sulfonic acids, sulfuric acid and Lewis acids, wherein said debutylation is carried out in the presence of water, a lower alcohol, or a mixture thereof.

2. A process as claimed in claim 1, wherein said debutylation is carried out at a temperature of from 100° to 200° C.

3. A process as claimed in claim 1, wherein said organic solvent has a boiling point of 100° C. or higher.

4. A process as claimed in claim 3, wherein said organic solvent is selected from an aromatic compound, a paraffin, and a paraffin mixture.

5. A process as claimed in claim 1, wherein said acid catalyst is present in an amount of from 0.1 to 20% by weight based on 3,3',5,5'-tetra-t-butyl-4,4'-dihydroxybiphenyl.

6. A process as claimed in claim 1, wherein said water, a lower alcohol, or a mixture thereof is present in an amount of from 0.1 to 10 times the weight of the acid catalyst.

7. A process as claimed in claim 1, wherein said debutylation is carried out under a pressure of from 100 Torr to 2 atm.

8. A process as claimed in claim 1, wherein said water, a lower alcohol, or a mixture thereof is added to the reaction system together with the acid catalyst.

9. A process as claimed in claim 3, wherein said debutylation is carried out while distilling the solvent.

10. A process as claimed in claim 9, wherein said debutylation is carried out while supplying a solvent heated to a temperature of from 100° to 250° C. to the reaction system.

11. A process as claimed in claim 10, wherein said solvent to be supplied has a temperature of from the reaction temperature up to a temperature higher than the reaction temperature by 50° C.

12. A process as claimed in claim 10, wherein said solvent to be supplied has a gaseous phase and is supplied by blowing into the reaction mixture.

13. A process for preparing 4,4'-dihydroxybiphenyl which comprises effecting debutylation of 3,3'5,5'-tetra-t-butyl-4,4'-dihydroxybiphenyl in an organic solvent in the presence of an acid catalyst selected from the group consisting of sulfonic acids, sulfuric acid, and Lewis acids, wherein said debutylation is initiated in the presence of water, a lower alcohol, or a mixture thereof.

14. A process as claimed in claim 1, wherein said lower alcohol is selected from the group consisting of methanol, ethanol, and propanol.

15. A process as claimed in claim 1, wherein said acid catalyst is selected from the group consisting of sulfonic acids and sulfuric acid.

16. A process as claimed in claim 1, wherein said acid catalyst is a Lewis acid.

17. A process as claimed in claim 15, wherein said sulfonic acid is selected from the group consisting of p-toluenesulfonic acid and benzenesulfonic acid.

18. A process as claimed in claim 16, wherein said Lewis acid is selected from the group consisting of aluminum trichloride, aluminum phenoxide compounds and aluminum alcoholates.

19. A process as claimed in claim 13, wherein said acid catalyst is selected from the group consisting of p-toluene-sulfonic acid, benzenesulfonic acid and sulfuric acid.

20. A process as claimed in claim 13, wherein said debutylation is conducted at a temperature of from 100° to 200° C.

* * * * *